United States Patent
Pepin et al.

(10) Patent No.: US 6,500,285 B2
(45) Date of Patent: *Dec. 31, 2002

(54) METHOD OF MAKING A CATHETER HAVING INTERLOCKING RIBBED BOND REGIONS

(75) Inventors: Henry John Pepin, Loretto, MN (US); Michael William Sterud, Prescott, WI (US); Anne Victoria Rossi, St. Michael, MN (US)

(73) Assignee: SciMed Life Systems, Inc., Maple Grove, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/378,867

(22) Filed: Aug. 23, 1999

(65) Prior Publication Data

US 2001/0045257 A1 Nov. 29, 2001

(51) Int. Cl.[7] .................. A61M 25/16; B32B 31/04
(52) U.S. Cl. .................. 156/86; 156/158; 156/294; 604/535
(58) Field of Search .................. 604/533, 534, 604/535, 523; 156/158, 294, 86, 304.5, 304.6

(56) References Cited

U.S. PATENT DOCUMENTS

| | | | |
|---|---|---|---|
| 2,185,741 A | 1/1940 | Sorg et al. | 138/61 |
| RE25,788 E | 6/1965 | Sheridan | 128/348 |
| 3,318,335 A | 5/1967 | Heller | 138/121 |
| 3,348,544 A | 10/1967 | Braun | 128/214.4 |
| 3,416,531 A | 12/1968 | Edwards | 128/348 |
| 3,470,869 A | 10/1969 | Fenton et al. | 128/2 |

(List continued on next page.)

FOREIGN PATENT DOCUMENTS

| | | |
|---|---|---|
| EP | 0 180 348 B1 | 5/1986 |
| EP | 0 555 088 A2 | 8/1993 |
| EP | 0 555 088 A3 | 8/1993 |
| EP | 0 437 291 B1 | 12/1993 |
| EP | 0 824 930 A2 | 2/1998 |
| EP | 0 852 955 A2 | 7/1998 |
| FR | 2 656 824 A1 | 7/1991 |
| GB | 2 187 670 A | 9/1987 |
| WO | WO 92/15356 | 9/1992 |
| WO | WO 96/20750 A1 | 7/1996 |
| WO | WO 98/25658 A1 | 6/1998 |

OTHER PUBLICATIONS

Johnson, R.W., "Paste Extrusion of Filled TFE–Fluorocarbon Resin For Wire Insulations," *SPE Journal*, Feb. 1961, pp. 151–154.

*Primary Examiner*—Michael W. Ball
*Assistant Examiner*—Barbara J Musser
(74) *Attorney, Agent, or Firm*—Crompton, Seager & Tufte, LLC

(57) ABSTRACT

A method of bonding a first tubular member to a second tubular member to form a catheter shaft. The method comprising the step of providing a first tubular member including a distal end, a proximal end, and a lumen extending between the distal end and the proximal end thereof. The method further including the step of providing a second tubular member including a distal end, a proximal end, and a lumen extending between the distal end and the proximal end thereof. The method further including the steps of inserting a joining portion of the first tubular member into a joining portion of the second tubular member and applying heat the joining portions.

23 Claims, 3 Drawing Sheets

U.S. PATENT DOCUMENTS

| | | | |
|---|---|---|---|
| 3,485,234 A | 12/1969 | Stevens | 128/2 |
| 3,720,210 A | 3/1973 | Diettrich | 128/214.4 |
| 3,725,522 A | 4/1973 | Sheridan et al. | 264/138 |
| 3,752,510 A | 8/1973 | Windischman et al. | 285/344.4 |
| 3,865,666 A | 2/1975 | Shoney | 156/245 |
| 3,873,391 A | 3/1975 | Plauka et al. | 156/258 |
| 3,914,002 A | 10/1975 | Berliner et al. | 339/16 R |
| 3,950,052 A | 4/1976 | Walter et al. | 339/8 R |
| 3,959,429 A | 5/1976 | Benning | 264/155 |
| 3,972,548 A | 8/1976 | Roseen | 285/381 |
| 3,985,601 A | 10/1976 | Panagrossi | 156/229 |
| 3,989,571 A | 11/1976 | Harautuneian | 156/250 |
| 4,085,185 A | 4/1978 | Adair | 264/248 |
| 4,093,484 A | 6/1978 | Harrison et al. | 156/244.13 |
| 4,154,244 A | 5/1979 | Becker et al. | 128/349 B |
| 4,191,185 A | 3/1980 | Lemieux | 128/214.4 |
| 4,198,983 A | 4/1980 | Becker et al. | 128/349 B |
| 4,207,900 A | 6/1980 | Patel et al. | 128/349 B |
| 4,210,478 A | 7/1980 | Shoney | 156/242 |
| 4,284,459 A | 8/1981 | Patel et al. | 156/245 |
| 4,328,056 A | 5/1982 | Snooks | 156/242 |
| 4,354,495 A | 10/1982 | Bodicky | 128/348 |
| 4,385,635 A | 5/1983 | Ruiz | 128/658 |
| 4,489,961 A | 12/1984 | Laidig | 285/116 |
| 4,509,877 A | 4/1985 | Sobin et al. | 403/41 |
| 4,511,163 A | 4/1985 | Harris et al. | 285/177 |
| 4,531,943 A | 7/1985 | Van Tassel et al. | 604/280 |
| 4,557,781 A | 12/1985 | Hoppie | 156/245 |
| 4,592,749 A | 6/1986 | Ebling et al. | 604/283 |
| 4,596,563 A | 6/1986 | Pande | 604/264 |
| 4,602,808 A | 7/1986 | Herron et al. | 285/45 |
| 4,636,272 A | 1/1987 | Riggs | 156/158 |
| 4,636,346 A | 1/1987 | Gold et al. | 264/139 |
| 4,655,762 A | 4/1987 | Rogers | 604/905 |
| 4,690,175 A | 9/1987 | Ouchi et al. | 138/131 |
| 4,735,620 A | 4/1988 | Ruiz | 604/281 |
| 4,737,219 A | 4/1988 | Taller et al. | 156/215 |
| 4,753,765 A | 6/1988 | Pande | 264/149 |
| 4,778,550 A | 10/1988 | Barton et al. | 156/211 |
| 4,806,182 A | 2/1989 | Rydell et al. | 156/211 |
| 4,826,480 A | 5/1989 | Diaz et al. | 604/280 |
| 4,838,269 A | 6/1989 | Robinson et al. | 128/344 |
| 4,838,879 A | 6/1989 | Tanabe et al. | 604/280 |
| 4,842,590 A | 6/1989 | Tanabe et al. | 604/282 |
| 4,863,441 A | 9/1989 | Lindsay et al. | 604/280 |
| 4,863,442 A * | 9/1989 | DeMello et al. | 604/282 |
| 4,874,373 A | 10/1989 | Luther et al. | 604/164 |
| 4,886,506 A | 12/1989 | Lovgren et al. | 604/280 |
| 4,950,257 A | 8/1990 | Hibbs et al. | 604/265 |
| 4,959,067 A | 9/1990 | Muller | 606/190 |
| 4,960,412 A | 10/1990 | Fink | 604/167 |
| 5,017,259 A * | 5/1991 | Kohsai | 156/294 |
| 5,035,686 A | 7/1991 | Crittenden et al. | 604/96 |
| 5,041,095 A | 8/1991 | Littrell | 604/167 |
| 5,078,702 A | 1/1992 | Pomeranz | 604/280 |
| 5,085,645 A | 2/1992 | Purdy et al. | 604/167 |
| 5,125,903 A | 6/1992 | McLaughlin et al. | 604/167 |
| 5,125,913 A | 6/1992 | Quackenbush | 604/264 |
| 5,129,887 A | 7/1992 | Euteneuer et al. | 606/194 |
| 5,143,409 A | 9/1992 | Lalikos | 285/116 |
| 5,160,559 A | 11/1992 | Scovil et al. | 156/73.6 |
| 5,163,431 A | 11/1992 | Griep | 604/282 |
| 5,167,647 A | 12/1992 | Wijkamp et al. | 604/281 |
| 5,176,660 A | 1/1993 | Truckai | 604/282 |
| 5,180,376 A | 1/1993 | Fischell | 604/282 |
| 5,181,750 A | 1/1993 | Reum | 285/38 |
| 5,190,529 A | 3/1993 | McCrory et al. | 604/175 |
| 5,201,723 A | 4/1993 | Quinn | 604/264 |
| 5,217,555 A | 6/1993 | Franklin, III et al. | 156/156 |
| 5,221,270 A | 6/1993 | Parker | 604/282 |
| 5,222,949 A | 6/1993 | Kaldany | 604/282 |
| 5,224,939 A | 7/1993 | Holman et al. | 604/283 |
| 5,226,898 A | 7/1993 | Gross | 604/243 |
| 5,234,416 A | 8/1993 | Macaulay et al. | 604/282 |
| 5,240,537 A | 8/1993 | Bodicky | 156/244.13 |
| 5,244,619 A | 9/1993 | Burnham | 264/173 |
| 5,248,305 A | 9/1993 | Zdrahala | 604/280 |
| 5,254,107 A | 10/1993 | Soltesz | 604/282 |
| 5,279,596 A | 1/1994 | Castaneda et al. | 604/282 |
| 5,300,032 A | 4/1994 | Hibbs et al. | 604/164 |
| 5,308,342 A | 5/1994 | Sepetka et al. | 604/282 |
| 5,312,356 A | 5/1994 | Engelson et al. | 604/164 |
| 5,318,032 A | 6/1994 | Lonsbury et al. | 128/658 |
| 5,330,444 A | 7/1994 | Webler et al. | 604/265 |
| 5,330,449 A | 7/1994 | Prichard et al. | 604/282 |
| 5,358,493 A | 10/1994 | Schweich, Jr. et al. | 604/264 |
| 5,376,077 A | 12/1994 | Gomringer | 604/167 |
| 5,380,301 A | 1/1995 | Prichard et al. | 604/281 |
| 5,395,332 A | 3/1995 | Ressemann et al. | 604/96 |
| 5,403,292 A | 4/1995 | Ju | 604/282 |
| 5,423,774 A | 6/1995 | Fischell et al. | 604/282 |
| 5,466,230 A | 11/1995 | Davila | 604/256 |
| 5,507,728 A | 4/1996 | Erskine | 604/164 |
| 5,509,910 A | 4/1996 | Lunn | 604/280 |
| 5,514,108 A | 5/1996 | Stevens | 604/280 |
| 5,533,988 A | 7/1996 | Dickerson et al. | 604/282 |
| 5,545,151 A | 8/1996 | O'Connor et al. | 604/282 |
| 5,558,635 A | 9/1996 | Cannon | 604/49 |
| 5,558,652 A | 9/1996 | Henke | 604/280 |
| 5,569,218 A | 10/1996 | Berg | 604/280 |
| 5,584,821 A | 12/1996 | Hobbs | 604/280 |
| 5,599,319 A | 2/1997 | Stevens | 604/264 |
| 5,695,467 A | 12/1997 | Miyata et al. | 604/96 |
| 5,762,637 A | 6/1998 | Berg et al. | 604/264 |
| 5,770,139 A | 6/1998 | Kinghorn et al. | 264/230 |
| 5,803,510 A | 9/1998 | Dorsey, III | 285/148.23 |
| 5,820,612 A | 10/1998 | Berg | 604/282 |
| 5,820,614 A * | 10/1998 | Berg | 604/282 |
| 5,897,537 A | 4/1999 | Berg et al. | 604/282 |
| 6,152,914 A * | 12/2000 | Van De Kerkhof et al. | 604/533 |

* cited by examiner

METHOD OF MAKING A CATHETER HAVING INTERLOCKING RIBBED BOND REGIONS

FIELD OF THE INVENTION

The present invention relates generally to catheters for performing medical procedures. More particularly, the present invention relates to guide catheters for use in angioplasty procedures.

BACKGROUND OF THE INVENTION

Intravascular diseases are commonly treated by relatively non-invasive techniques such as percutaneous transluminal angioplasty (PTA) and percutaneous transluminal coronary angioplasty (PTCA). These angioplasty techniques typically involve the use of a balloon catheter. In these procedures, a balloon catheter is advanced through the vasculature of a patient such that the balloon is positioned proximate a restriction in a diseased vessel. The balloon is then inflated and the restriction in the vessel is opened.

The most widely used form of angioplasty makes use of a guide catheter positioned within the vascular system of a patient. The guide catheter assists in transporting the balloon dilation catheter to the restriction in the diseased vessel. During this procedure, the distal end of the guide catheter is typically inserted into the femoral artery located near the groin of the patient. The guide catheter is urged through the vasculature of the patient until its distal end is proximate the restriction. In many cases, the distal end of the guide catheter is positioned in the ostium of the coronary artery. The balloon catheter may then be fed through a lumen in the guide catheter.

It is desirable that a guide catheter incorporate a level of rigidity which will allow it to be passed through the vascular system without folding or buckling. To assist in directing the distal tip of the guide catheter to the coronary ostium of the patient, the distal portion of the guide catheter may include one or more bends. The distal tip of the guide catheter is typically formed from relatively soft, flexible material to avoid trauma to arterial vessels, and allow flexing of the distal tip to aid the guide catheter in traversing desired arterial branches.

In some applications, it is desirable to form a guide catheter by bonding together two or more tubular sections in order to achieve a more rigid proximal portion and more flexible distal portion. It may also be desirable to have the distal portion of the guide catheter shaft be comprised of one or more tubular sections which are adapted to be formed into a curved shape. As described above, these curves aid in directing the distal tip of the guide catheter to the coronary ostium of a patient. In some embodiments, it is desirable to have a distal portion of the elongate shaft which can be heated and bent to a desired shape, then allowed to cool. By way of a second example, it may be desirable to include one or more tubular sections having a reinforcement braid, and one or more additional tubular sections having no braid. A braid or other reinforcement member is used to strengthen the tubular section and increase torque transmission. When a guide catheter is comprised of more than one generally tubular section, these sections are joined together at joints where the distal end of a first tubular section is affixed to the proximal end of a second tubular section.

SUMMARY OF THE INVENTION

The present invention relates generally to catheters for performing medical procedures. More particularly, the present invention relates to guide catheters for use in an angioplasty procedure. A guide catheter in accordance with the present invention includes an elongate shaft. A hub may be affixed to the proximal end of the elongate shaft and an atraumatic tip may be affixed to the distal end of the elongate shaft. The elongate shaft is preferably comprised of more than one generally tubular section.

A method of bonding tubular members in accordance with the present invention may begin with the step of forming a joining region on the distal portion of a first tubular member. The joining region preferably includes a plurality of ribs and a plurality of areas with a generally reduced diameter relative to the ribs. A variety of manufacturing methods may be used to form the ribs including material forming processes and material removal processes.

A method in accordance with the present invention includes the step of positioning a mandrel. so that at least a portion of its length is disposed inside the lumen of the first tubular member. The joining region of the first tubular member is then inserted into the lumen of a second tubular member. After the joining region of the first tubular member is inserted into the lumen of the second tubular member, the mandrel will be positioned so that at least a portion of the length thereof is disposed inside both the lumen of the first tubular member and the lumen of the second tubular member.

The assembled tubular members are then subjected to heat and pressure proximate the joining region of the first tubular member. A number of methods may be used to heat the tubular members, including convection, conduction and radiation. The second tubular member is thus bonded to the first tubular member at the joining region.

Having formed a bond, the assembly is then allowed to cool. The assembly may be submersed in a relatively cool fluid to speed cooling of the assembly. Examples of fluids which may be suitable for some applications include water and air. Relatively cool air may also be impinged onto the assembly. After the catheter assembly has cooled, the mandrel may be removed from the lumen of the catheter assembly.

An additional method in accordance with the present invention includes the step of positioning a shrink wrap sleeve over both tubular members in an area proximate the joining region of the first tubular member. After the sleeve is disposed about the tubular members, heat is applied to joining regions to form a bond. At an elevated temperature, the shrink wrap sleeve applies the pressure necessary to form the second tubular member around the joining region of the first tubular member. Having formed a bond, the assembly is then allowed to cool. After the assembly has cooled, the sleeve and the mandrel are removed.

An additional method in accordance with the present invention may be used to bond a hub to a tubular member. This method typically begins with the step of forming a bonding region on the tubular member proximate the proximal end thereof. The bonding region typically includes at least one rib and at least one area of generally reduced diameter relative to the rib diameter. The proximal portion of the tubular member is then positioned inside the cavity of a molding tool. Molten plastic is then injected into the cavity of the molding tool and allowed to cool.

DETAILED DESCRIPTION OF THE INVENTION

The following detailed description should be read with reference to the drawings, in which like elements in different drawings are numbered identically. The drawings, which are not necessarily to scale, depict selected embodiments and are not intended to limit the scope of the invention.

Examples of construction, materials, dimensions, and manufacturing processes are provided for selected elements. All other elements employ that which is known to those of skill in the field of the invention. Those skilled in the art will recognize that many of the examples provided have suitable alternatives which may be utilized.

Figure 1:
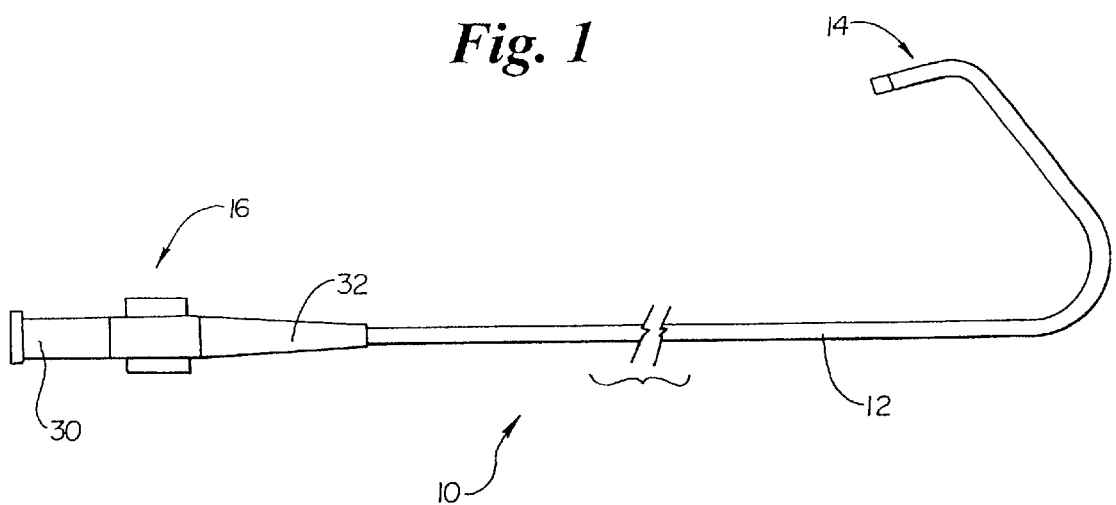
FIG. 1 is a plan view of a guide catheter in accordance with an exemplary embodiment of the present invention.

FIG. 1 is a plan view of a guiding catheter 10. Guiding catheter 10 includes an elongate shaft 12, a distal portion 14, and a proximal portion 16. Proximal portion 16 of catheter 10 includes a hub 30 and a strain relief 32. Hub 30 and strain relief 32 enable a physician to connect other devices to guiding catheter 10. Hub 30 and strain relief 32 also provide a convenient place for a physician to apply longitudinal or rotational forces in order to manipulate guiding catheter 10. Connected to the distal end of catheter 10 is a distal tip 20. In a preferred embodiment, distal tip 20 is generally softer and more flexible than elongate shaft 12.

Figure 2:
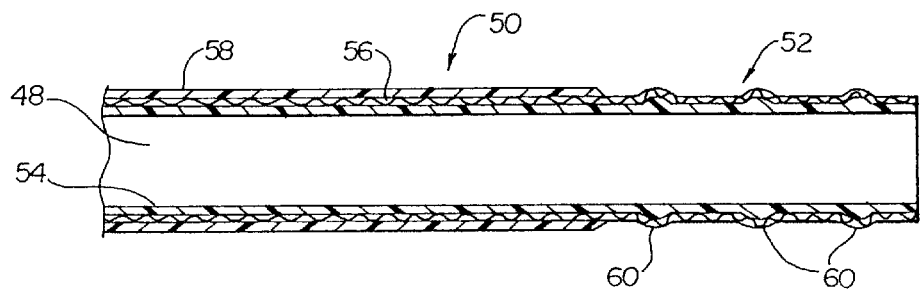
FIG. 2 is a sectional plan view of a tubular member having a joining region form thereon depicting raised ribs and reduced diameter portions therebetween.

Those of skill in the art will appreciate that for many applications of catheter 10, elongate shaft 12 is preferably comprised of more than one generally tubular section 50. For example, the distal portion of elongate shaft 12 may be comprised of one or more tubular sections 50 which are adapted to be formed into a curved shape. Curves disposed proximate the distal portion of elongate shaft 12 aid in directing the distal end of catheter 10 to the coronary ostium of a patient. In some embodiments, it is desirable to have a distal portion of elongate shaft 12 which can be heated and bent to a desired shape, then allowed to cool. By way of a second example, it may be desirable to include one or more tubular sections 50 having a reinforcement braid, and one or more additional tubular sections 50 having no braid. When elongate shaft 12 is comprised of more than one generally tubular section 50, these sections are joined together at joints where the distal end of a first tubular section 50 is affixed to the proximal end of a second tubular section 50. FIG. 2 is an enlarged sectional view of a preferred distal portion 14 of a tubular section 50 of the present invention having a joining region 52 and a lumen 48. Tubular section 50 is comprised of an inner tube 54 which is overlaid by a support member 56. An outer tube 58 overlays support member 56 and preferably terminates proximal to the joining region 52.

Joining region 52 of tubular section 50 includes a plurality of ribs 60 extending circumferentially around the shaft at spaced longitudinal positions. The joining region 52, including the ribs 60 and axial spaces therebetween, preferably has a smaller outside diameter than the shaft proximal thereto. The ribs have a slightly larger diameter than the axial regions therebetween.

A variety of manufacturing methods may be used to form joining region 52 and ribs 60 of tubular section 50 including material forming processes and material removal processes. Examples of material removal processes which may be acceptable in some applications include turning on a lathe and centerless grinding. An example of a material forming process which may be acceptable in some applications is forging by compressing joining region 52 of tubular section 50 in a heated tool of the desired shape.

In a preferred embodiment, inner tube 54 is comprised of PTFE (polytetrafluoroethylene). PTFE is a preferred material because it creates a smooth, low-friction surface for the passage of other devices through the catheter. Also in a preferred embodiment, support member 56 is a stainless steel wire, wound in a braided pattern around inner tube 54. Those with skill in the art will appreciate that other embodiments of support member 56 are possible without deviating from the spirit and scope of the present invention. For example, support member 56 may be comprised of a woven polymer fabric. By way of a second example, support member 56 may be comprised of polymer fibers wound in a braided pattern.

In a preferred embodiment, outer tube 58 is comprised of polyether block amide (PEBA). Polyether block amide is commercially available from Atochem Polymers of Birdsboro, Pa. under the trade name PEBAX. Outer tube 58 may be fabricated using an extrusion process. In this process, molten PEBA is extruded onto the combined layers of inner tube 54 and support member 56. When this process is used, the material of outer tube 58 fills any interstitial spaces in support member 56.

It is to be understood that other manufacturing processes can be used without departing from the spirit and scope of the present invention. Outer tube 58 may also be comprised of other materials without departing from the spirit of scope of this invention. Examples of materials which may be suitable in some applications include: polyethylene (PE), polypropylene (PP), polyvinylchloride (PVC), polyurethane, and polytetrafluoroethylene (PTFE).

As described previously, the material of distal tip 20 is preferably a relatively soft material. Distal tip 20 may be comprised of a material which is softer than the material of outer layer 56. In a preferred embodiment, both distal tip 20 and outer layer 56 are comprised of polyether block amide (PEBA). However, in this preferred embodiment, distal tip 20 is comprised of a PEBA material with a lower durometer than that of outer layer 56.

Those with skill in the art will appreciate that other embodiments of tubular section 50 are possible without deviating from the spirit or scope of the present invention. For example, tubular section 50 may include more or fewer component layers.

Figure 3:
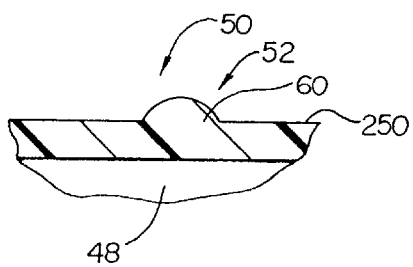
FIG. 3 is an enlarged partial sectional view of a rib portion on a catheter shaft.

FIG. 3 is an enlarged sectional view of an additional embodiment of a tubular section 50. In the embodiment of FIG. 3, tubular section 50 includes a wall 250 which is comprised of a first material. Tubular section 50 also includes a joining region 52 having a plurality of ribs 60. A variety of manufacturing methods may be used to form ribs 60 on joining region 52 of tubular section 50 including material forming processes and material removal processes. Examples of material removal processes which may be acceptable in some applications include turning on a lathe and centerless grinding. An example of a material forming process which may be acceptable in some applications is forging by compressing joining region 52 of tubular section 50 in a heated tool of the desired shape. Ribs 60 are preferably about 0.001 inches to about 0.006 inches in height relative to the reduced diameter longitudinal regions therebetween.

Figure 4:
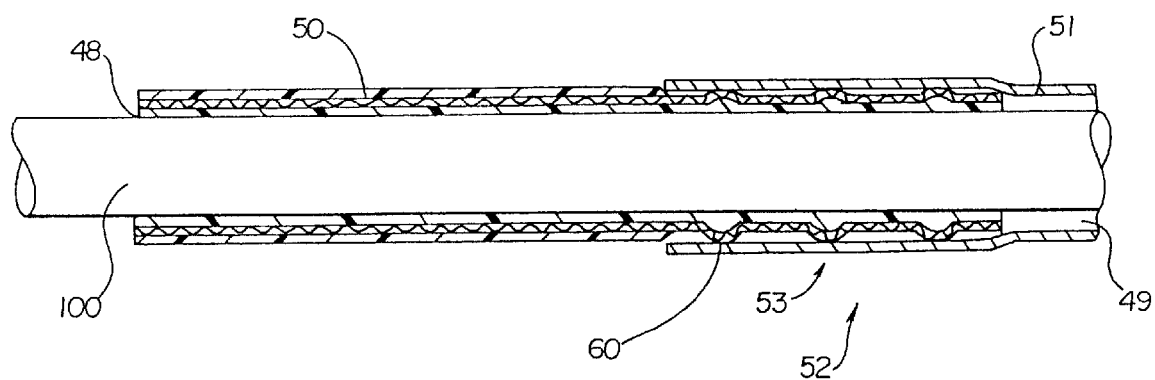
FIG. 4 is a sectional plan view of the tubular member of FIG. 2 with a second tubular member disposed over the joining region prior to bonding.

FIG. 4 is a plan view of an assembly including a first tubular member 50 and a second tubular member 51. Tubular members 50 and 51 include lumens 48 and 49, respectively. In FIG. 4, a mandrel 100 has been positioned so that at least a portion of its length is disposed inside lumens 48, 49 of tubular members 50, 51. Tubular member 50 includes bonding region 52 having a plurality of ribs 60. Tubular member 51 includes a joining region 53, which is a portion of the lumen wall over a selected length.

In FIG. 4, bonding region 52 of tubular member 50 has been inserted into bonding region 53 of tubular member 51. In a preferred embodiment of tubular member 51, the inner diameter of bonding region 53 is slightly flared to facilitate the insertion of bonding region 52 of tubular member 50. This flared diameter may be created using a heat forming process. Alternately, bonding region 52 of tubular member 50 may be press fit into bonding region 53 of tubular member 51 without first creating a flare.

A method of bonding tubular members in accordance with the present embodiment may be described making reference to FIG. 4. A preferred method begins with the step of forming joining region 52 and ribs 60 in tubular member 50. A variety of manufacturing methods may be used to form ribs 60 on tubular member 50 including material forming processes and material removal processes. Examples of material removal processes which may be acceptable in some applications include turning on a lathe and centerless grinding. An example of a material forming process which may be acceptable in some applications is forging by compressing joining region 52 of tubular member 50 in a heated tool of the desired shape.

A method in accordance with the present invention includes the step of positioning mandrel 100 so that at least a portion of its length is disposed inside lumen 48 of tubular member 50. In a preferred method, this step takes place after the formation of joining region 52 and ribs 60. Those of skill in the art will appreciate that the order of the steps in this method may be changed without deviating from the spirit and scope of the invention. For example, mandrel 100 may be positioned in lumen 48 of tubular member 50 prior to the formation of joining region 52 and ribs 60. Alternately, mandrel 100 may be positioned in lumen 48 of tubular member 50 after joining region 52 of tubular member 50 has been inserted into joining region 53 of tubular member 51.

In the next step of a preferred method, bonding region 52 of tubular member 50 is inserted into bonding region 53 of tubular member 51. A preferred method in accordance with the invention includes the step of flaring the inner diameter of tubular member 51 proximate bonding region 53. Bonding region 53 of tubular member 51 may be flared to facilitate the insertion of bonding region 52 of tubular member 50. A number of methods may be used to flare tubular member 51 proximate bonding region 53. In a method which may be suitable for some applications, the bonding region 53 of tubular member 51 is heated, then a mandrel is urged into lumen 49 of tubular member 51. To facilitate the flaring process, a portion of the mandrel has a diameter larger than the diameter of lumen 49 of tubular member 51. It should be noted that the mandrel may include steps and tapers. The distal end of tubular member 51 takes on the shape of the mandrel as a result of urging the mandrel into heated tubular member 51.

After bonding region 52 of tubular member 50 is inserted into bonding region 53 of tubular member 51, mandrel 100 will be positioned so that at least a portion of the length thereof is disposed inside both lumen 48 of tubular member 50 and lumen 49 of tubular member 51.

Having thus assembled tubular members 50, 51, heat and pressure are applied to joining regions 52, 53. A number of methods may be used to heat joining regions 52, 53 including convection, conduction and radiation. An example of heating with radiant energy is directing infrared energy from an infrared heat source at joining regions 52 and 53. Infrared energy sources suitable for this process are commercially available from Research Incorporated of Minnetonka, Minn. A second example of heating with radiant energy is exposing the regions to be heated to radio frequency energy.

An example of heating with convection includes directing a flow of hot air from a hot air gun so that it impinges on joining regions 52 and 53. Hot air guns suitable for this application are commercially available from Leister Elektro-Geratebau of Lucerne, Switzerland. A second example of heating with convection includes placing the portion being heated in a temperature chamber. Temperature chambers suitable for this process are commercially available from Thermotron Corporation of New Holland, Mich.

An example of heating with conduction is placing a heated tool in direct contact with the outside diameter of joining region 53 and/or the inside diameter of joining region 52. Suitable heated tools may be comprised of a number of materials including stainless steel. Electric heaters suitable for heating a heated tool are commercially available from Watlow Incorporated of St. Louis, Mo.

Pressure may be applied to joining regions 52, 53 via a fluid under pressure or via a solid tool adapted to apply pressure to the outer diameter of joining region 53. Pressure may be applied using a fluid by positioning joining regions 52, 53 within a pressure vessel, then pressurizing the vessel with a fluid. In this example, the fluid could be air, water, alcohol, nitrogen gas, etc.

Having formed a bond, the assembly is then allowed to cool. The assembly may be submersed in a relatively cool fluid to speed cooling of the assembly. Examples of fluids which may be suitable for some applications include water and air. Relatively cool air may also be impinged onto the assembly. Cold air generators suitable for this purpose are commercially available from ITW Vortec of Cincinnati, Ohio and Exair Corporation of Cincinnati, Ohio.

After the catheter assembly has cooled, mandrel 100 may be removed from the lumen of the catheter assembly. In a preferred method, the outer surface of mandrel 100 includes polytetrafluoroethylene (PTFE). PTFE is preferred because it provides a substantially non-stick surface. This substantially non-stick surface aids in the removal of mandrel 100 from the lumen of the catheter assembly.

Figure 5:
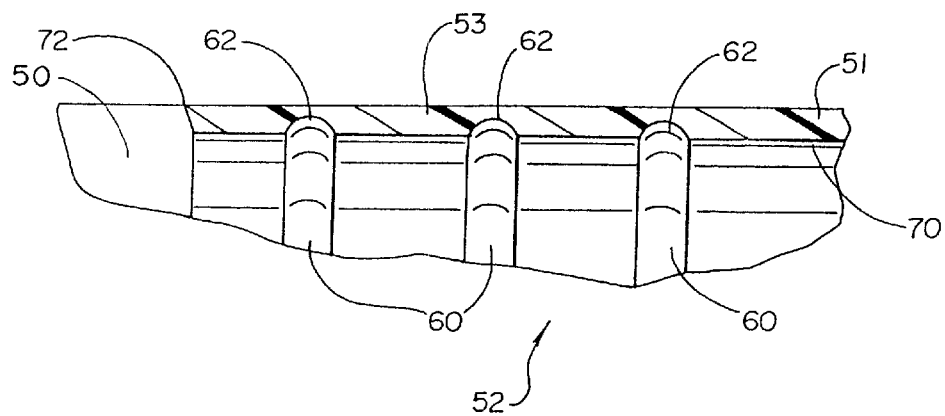
FIG. 5 is a sectional plan view of a first tubular member which has been bonded to a second tubular member depicting the second tubular member conforming to the ribs and reduced diameter portions therebetween.

FIG. 5 is a partial plan view illustrating joining regions 52, 53 after the completion of the bonding process. In FIG. 5 tubular member 51 is shown in cross-section and tubular member 50 is not. As seen in FIG. 5, the material of tubular member 51 has conformed to the shape of bonding area 52 of tubular member 50. As a result of the joining process, joining region 53 of tubular member 51 includes a groove 62 corresponding to each rib 60 of tubular member 50. The interlocking geometry of ribs 60 and grooves 62 increases the mechanical strength of the resulting joint. Also as a result of the joining process, a lap joint heat bond 70 has been formed between the inner diameter of tubular member 51 and the outer diameter of tubular member 50. Also as a result of the joining process, a butt joint heat bond 72 has been formed between the proximal end of tubular member 51 and the distal end of tubular member 50.

Figure 6:
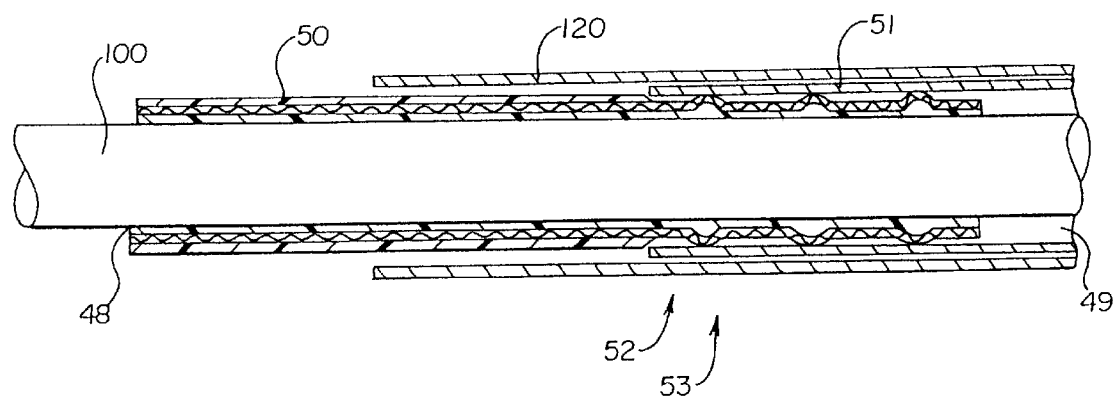
FIG. 6 is a sectional plan view of the tubular member of FIG. 2 with a second tubular member disposed over the joining region and a heat shrink sleeve disposed over the assembly prior to bonding.

An additional method in accordance with the present invention is illustrated in FIG. 6. This method includes the step of positioning a sleeve 120 over both tubular members 50, 51 in an area proximate joining area 53. In a preferred embodiment, sleeve 120 is comprised of heat shrinkable polytetrafluoroethylene (PTFE). PTFE is preferred because it provides a substantially non-stick surface.

In a preferred embodiment, sleeve 120 is comprised of PTFE heat shrink tubing. Suitable PTFE heat shrink tubing is commercially available from Zeus Industries of Orangeburg, S.C. and Raychem Corporation of Menlo Park, Calif. When sleeve 120 is comprised of shrink tubing, the step of shrinking sleeve 120 may be included in a method in accordance with the present invention. A number of methods may be used to shrink sleeve 120 without departing from the spirit and scope of the present invention, including those steps previously described in conjunction with FIG. 5. In a preferred method, hot air is first impinged upon sleeve 120 causing it to shrink. Hot air guns suitable for this application are commercially available from Leister Elektro-Geratebau of Lucerne, Switzerland.

After sleeve 120 is disposed about tubular members 50, 51, heat and pressure are applied to joining regions 52, 53 to form a bond. Having formed a bond, the assembly is then allowed to cool. The assembly may be submersed in a relatively cool fluid to speed cooling of the assembly. Examples of fluids which may be suitable for some applications include water and air. Relatively cool air may also be impinged onto the assembly. Cold air generators suitable for this purpose are commercially available from ITW Vortec of Cincinnati, Ohio and Exair Corporation of Cincinnati, Ohio. After the assembly has cooled, sleeve 120 is removed. This may be accomplished by scoring sleeve 120 with a cutting tool, and peeling it away from the catheter assembly.

The mandrel 100 is then removed from the lumen of the catheter assembly. In a preferred method, the outer surface of mandrel 100 includes polytetrafluoroethylene (PTFE). PTFE is preferred because it provides a substantially non-stick surface. This substantially non-stick surface aids in the removal of mandrel 100 from the lumen of the catheter assembly.

Figure 7:
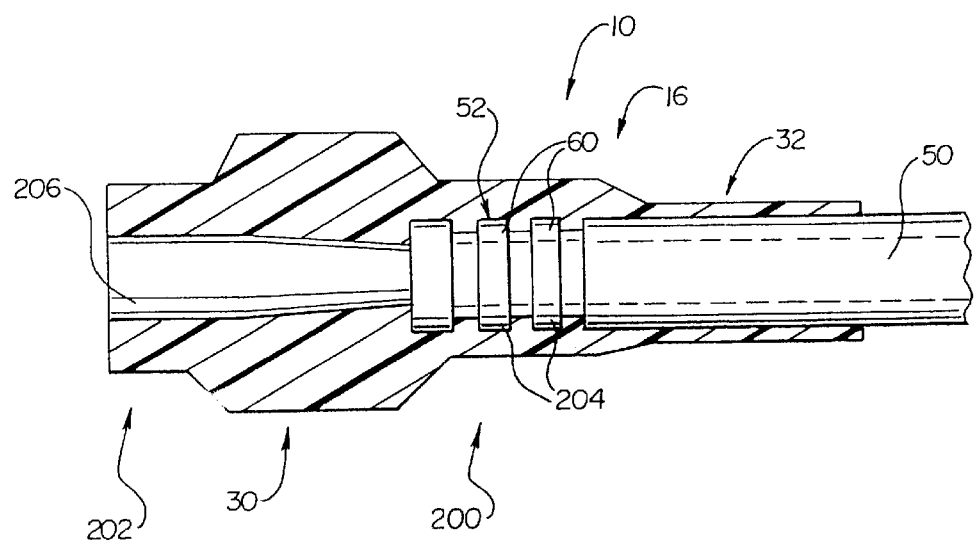
FIG. 7 is a plan view of a hub assembly in accordance with an exemplary embodiment of the present invention incorporating ribs and reduced diameter portions on a joining region.

FIG. 7 is a plan view of the proximal portion 16 of a catheter 10 in accordance with the present invention. Catheter 10 of FIG. 7, includes a tubular member 50 having a bonding region 52. Catheter 10 also includes a strain relief 32 disposed about a portion of proximal portion 16 of catheter 10. Catheter 10 also includes a hub 30 having a bonding region 200, a coupling region 202, and a strain relief region 32. As shown in FIG. 7, bonding region 200 of hub 30 is generally disposed about and bonded to bonding region 52 of tubular member 50.

Bonding region 52 of tubular member 50 includes a plurality of ribs 60. Bonding region 200 of hub 30 includes a plurality of grooves 204 corresponding to ribs 60 of tubular member 50. As shown in FIG. 7, ribs 60 of tubular member 50 are generally disposed in grooves 204 of hub 30. The interlocking geometry of ribs 60 and grooves 204 increases the mechanical strength of the resulting joint. Coupling region 202 of hub 30 is adapted to form a mating connection with other devices. Specifically, coupling region 202 is adapted to form a connection which places another device in fluid communication with a lumen 206 of hub 30. In one embodiment of the present invention, coupling region 202 includes a leur fitting.

A method of creating a hub bonded to a tubular member in accordance with the present invention may be described making reference to FIG. 7. A preferred method, begins with the step of forming ribs 60 in joining region 52 of tubular member 50. A variety of manufacturing methods may be used to form ribs 60 on tubular section 60 including material forming processes and material removal processes. Examples of material removal processes which may be acceptable in some applications include turning on a lathe and centerless grinding. An example of a material forming process which may be acceptable in some applications is forging ribs by compressing joining region 52 of tubular member 50 in a heated tool of the desired shape.

The proximal portion of tubular member 50 including joining region 52 is then positioned inside a mold cavity and molten plastic is injected into the mold. The molten plastic surrounds joining region 52 of tubular member 50 forming grooves 204 corresponding to ribs 60. The molten plastic is then allowed to cool and solidify forming hub 30. Once hub 30 has been formed, it is removed from the tool. The interlocking geometry of ribs 60 and grooves 204 increases the mechanical strength of the resulting joint.

Having thus described the preferred embodiments of the present invention, those of skill in the art will readily appreciate that yet other embodiments may be made and used within the scope of the claims hereto attached.

Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. A method of bonding a first tubular member to a second tubular member to form a catheter shaft, the method comprising the steps of:

providing a first tubular member including a distal end, a proximal end, and a lumen extending between the distal end and the proximal end thereof;

providing a second tubular member including a distal end, a proximal end, and a lumen extending between the distal end and the proximal end thereof;

the second tubular member including a joining region proximate the proximal end thereof;

forming a bonding region in the first tubular member proximate the distal end thereof; the bonding region having an outer diameter that is less than the outer diameter of the first tubular member at a location proximal to the bonding region, and the bonding region including a generally reduced diameter portion having a substantially constant circumference and at least two ribs disposed adjacent the reduced diameter portion, the ribs having an outer diameter that is larger that the outer diameter of reduced diameter portion and smaller than the outer diameter of the first tubular member at a location proximal to the bonding region;

inserting a mandrel of substantially constant diameter into the lumen of the first tubular member proximate the distal end thereof;

inserting the distal end of the first tubular member into the lumen of the second tubular member so that the joining region of the second tubular member is disposed about the bonding region of the first tubular member;

heating the joining region of the second tubular member, wherein a bond is formed between the joining region of the second tubular member and the bonding region of the first tubular member such that a bonded member is formed having an outside diameter that is substantially the same for at least a portion of the length of the catheter shaft, including the bonding region and a length both proximal and distal of the bonding region; and removing the mandrel from the lumen of the first tubular member.

2. The method of claim 1, further including the steps of providing a sleeve having a lumen and positioning the sleeve so that it overlays the joining region of the second tubular member.

3. The method of claim 1, further including the steps of providing a sleeve comprised of shrink tubing, positioning the sleeve so that it overlays the joining region of the second tubular member, and heating the sleeve so that it shrinks.

4. The method of claim 1, further including the step of cooling the joining region of the second tubular member.

5. The method of claim 1, further including the step of heating the bonding region of the first tubular member.

6. The method of claim 1, further including the step of applying pressure to an outer surface of the joining region of the second tubular member.

7. The method of claim 1, further including the step of flaring the proximal end of the second tubular member.

8. The method of claim 1, wherein the first tubular member is comprised of a thermoplastic material.

9. The method of claim 1, wherein the second tubular member is comprised of a thermoplastic material.

10. The method of claim 1, wherein the first tubular member is comprised of polyether block amide.

11. The method of claim 1, wherein an outer diameter of the mandrel is substantially equal to a diameter of the lumen of the first tubular member.

12. The method of claim 1, wherein a diameter of the lumen of the second tubular member is substantially equal to a diameter of the lumen of the first tubular member.

13. The method of claim 1, wherein an outer diameter of the first tubular member is substantially equal to an outer diameter of the second tubular member after the second tubular member has been bonded to the first tubular member.

14. The method of claim 1, wherein the step of forming the bonding region of the first tubular member includes removing material from the first tubular member.

15. A method of bonding a first tubular member to a second tubular member to form a catheter shaft, the method comprising the steps of:

providing a first tubular member including a distal end, a proximal end, and a lumen extending between the distal end and the proximal end thereof;

forming a bonding region proximate the distal end of the first tubular member, the bonding region having a substantially constant basic outer diameter generally less than the outer diameter of the first tubular member and at least two ribs having an outer diameter greater than the basic diameter of the bonding region and less than the outer diameter of the first tubular member;

inserting a mandrel of substantially constant diameter into the lumen of the first tubular member;

providing a second tubular member including a distal end, a proximal end, and a lumen extending between the distal end and the proximal end thereof;

the second tubular member including a joining region proximate the proximal end thereof;

inserting the distal end of the first tubular member into the lumen of the second tubular member so that the second tubular member is disposed about the bonding region of the first tubular member;

placing a sleeve over the joining region of the second tubular member;

heating the bonding region of the first tubular member and the joining region of the second tubular member; and removing the mandrel from the lumen of the first tubular member such that a bonded member is formed having an outside diameter that is substantially the same for at least a portion of the length of the catheter shaft, including the bonding region and a length both proximal and distal of the bonding region.

16. The method of claim 15, wherein the step of forming a bonding region includes removing material from the first tubular member.

17. The method of claim 15, wherein the step of forming a bonding region includes deforming the first tubular member.

18. The method of claim 15, further including the step of cooling the joining region of the second tubular member.

19. The method of claim 15, further including the step of applying pressure to the joining region of the second tubular member.

20. The method of claim 15, wherein the first tubular member is comprised of a thermoplastic material.

21. The method of claim 15, wherein the second tubular member is comprised of a thermoplastic material.

22. The method of claim 15, wherein the first tubular member is comprised of polyether block amide.

23. A method of bonding a first tubular member to a second tubular member to form a catheter shaft, the method comprising the steps of:

providing a first tubular member including a distal end, a proximal end, and a lumen extending between the distal end and the proximal end thereof;

providing a second tubular member including a distal end, a proximal end, and a lumen extending between the distal end and the proximal end thereof;

the second tubular member including a joining region proximate the proximal end thereof;

providing a shrink tube sleeve;

forming a bonding region in the first tubular member proximate the distal end thereof; the bonding region having an outer diameter that is less than the outer diameter of the first tubular member at a location proximal to the bonding region, and the bonding region including a generally reduced diameter portion having a substantially constant circumference and at least two ribs disposed adjacent the reduced diameter portion, the ribs having an outer diameter that is larger that the outer diameter of reduced diameter portion and smaller than the outer diameter of the first tubular member at a location proximal to the bonding region;

inserting a mandrel of substantially constant diameter into the lumen of the first tubular member proximate the distal end thereof;

inserting the distal end of the first tubular member into the lumen of the second tubular member so that the joining region of the second tubular member is disposed about the bonding region of the first tubular member;

positioning the shrink tube sleeve so that it overlays the joining region of the second tubular member;

applying pressure and heat to an outer surface of the joining region of the second tubular member, wherein a bond is formed between the joining region of the second tubular member and the bonding region of the first tubular member;

cooling the joining region of the second tubular member; and removing the mandrel from the lumen of the first tubular member such that a bonded member is formed having an outside diameter that is substantially the same for at least a portion of the length of the catheter shaft, including the bonding region and a length both proximal and distal of the bonding region.

* * * * *